United States Patent [19]

Jonsson et al.

[11] Patent Number: 4,555,251
[45] Date of Patent: Nov. 26, 1985

[54] PROCESS FOR THE SEPARATION OF GASEOUS MIXTURES USED IN STERILIZATION PROCESSES

[75] Inventors: Ernst U. Jonsson, Lund; Sten-Borje Lindqvist, Veberod; Roland V. Wimmerstedt, Lund, all of Sweden

[73] Assignee: Gambro Lundia AB, Sweden

[21] Appl. No.: 605,585

[22] Filed: Apr. 30, 1984

[30] Foreign Application Priority Data

May 6, 1983 [SE] Sweden ................................ 8302611

[51] Int. Cl.[4] .............................................. B01D 53/14
[52] U.S. Cl. .......................................... 55/48; 55/51; 55/89; 55/94; 422/34; 549/541
[58] Field of Search ................... 55/46, 48, 51, 89, 93, 55/94, 223; 422/30, 31, 34; 549/538, 541

[56] References Cited

U.S. PATENT DOCUMENTS

| | | | |
|---|---|---|---|
| 3,165,539 | 1/1965 | Lutz | 55/51 |
| 3,745,092 | 7/1973 | Vanderwater | 203/42 |
| 3,766,714 | 10/1973 | Cunningham et al. | 55/48 |
| 3,856,484 | 12/1974 | Cocuzza et al. | 55/48 |
| 3,948,621 | 4/1976 | Cocuzza et al. | 55/48 X |
| 3,989,461 | 11/1976 | Skocypec et al. | 422/34 X |
| 4,130,393 | 12/1978 | Fox | 422/31 |

FOREIGN PATENT DOCUMENTS 2200926  8/1972  Fed. Rep. of Germany .

Primary Examiner—Charles Hart
Attorney, Agent, or Firm—Lerner, David, Littenberg, Krumholz & Mentlik

[57] ABSTRACT

Processes and apparatus for the separation of gaseous mixtures used in sterilization processes are disclosed, particularly in which the gaseous mixtures include ethylene oxide and a relative inert secondary gas component, such as various chlorofluorocarbons. The processes disclosed include providing water as a solvent for the ethylene oxide, mixing the gaseous mixture with the water to produce a liquid phase comprising the ethylene oxide at least partially dissolved in the water, and the gas phase comprising the secondary gaseous component which is less soluble in the water than the ethylene oxide, removing the gas phase from the liquid phase for further processing, separating the ethylene oxide from the water in the liquid phase, and recycling the water for subsequent use as solvent. The apparatus disclosed include a water tank, a pump for mixing the gaseous mixture with the water to produce a liquid phase of the ethylene oxide at least partially dissolved in the water, and a gas phase, a separating tank for separating the gas and liquid phase, a stripper for separating the ethylene oxide from the water, and a recycle circuit for recycling the water back to the water tank for further use as solvent.

16 Claims, 1 Drawing Figure

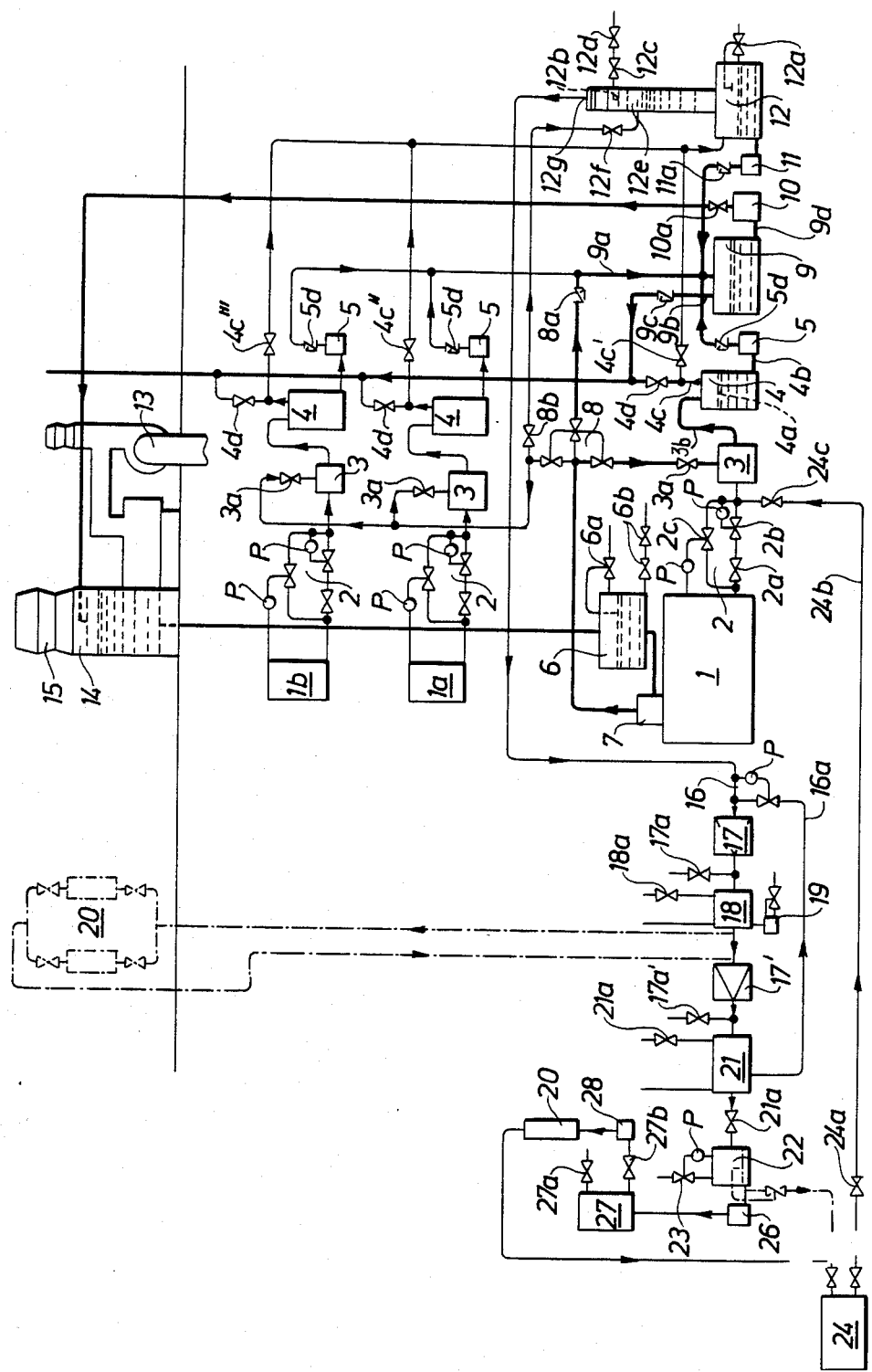

PROCESS FOR THE SEPARATION OF GASEOUS MIXTURES USED IN STERILIZATION PROCESSES

FIELD OF THE INVENTION

The present invention relates to processes for separating gaseous mixtures. More particularly, the present invention relates to processes for separating gaseous mixures generally used in sterilization processes, and most particularly gaseous mixtures of ethylene oxide with other gaseous constituents, such as carbon dioxide and/or various chlorofluorocarbons which are relatively inert from the point of view of such sterilization processes.

BACKGROUND OF THE INVENTION

It is well known that ethylene oxide ($C_2H_4O$) can be used in pure form for the sterilization of heat-sensitive plastics. Preferably, however, it is used in admixture with one or more inert gases, such as carbon dioxide or various chlorofluorocarbons, such as freon 11 ($CFCl_3$) or freon 12 ($CCl_2F_2$). In a number of these mixtures which are now being marketed the inert gas serves only as a complement so as to render the mixture non-flammable, and thus also non-explosive in air.

An example of a customary sterilizing gas mixture of this type is one including about 12% by weight ethylene oxide and about 88% by weight freon 12. The reason for using such a composition is that ethylene oxide is non-flammable in air in admixture with freon 12, if the admixture contains below approximately 14 to 15% by weight of the ethylene oxide. Since ethylene oxide and freon 12 have approximately equal costs of manufacture, it would be desirable from an economic point of view to recover both of these components, or at least the major component, i.e. the freon.

It is known, as shown for example in U.S. Pat. No. 4,249,917, that these two components can be recovered simultaneously by dissolving them both in a common solvent. However, in view of the need for simultaneous dissolution of both such components in this system, great demands are placed upon the solvent to be so utilized.

In accordance with U.S. Pat. No. 4,112,054 the ethylene oxide is removed from a gaseous mixture by a process which includes its conversion to ethylene glycol and polyethylene glycol. In the case of this process, however, it is also only very special solvents which can be used.

It is also known, as shown for example in U.S. Pat. No. 3,372,980, that the gaseous mixture may be re-used as such, but only in connection with very accurate control of its composition. In normal sterilization processes, however, the gaseous mixture will sooner or later become diluted with an amount of air such that it will no longer be safe to utilize. In such situations it then becomes necessary to either substitute a new gaseous mixture, or regenerate the gaseous mixture in some way.

Finally, it is also well known that ethylene oxide is soluble in water as mentioned, for example, in U.S. Pat. No. 4,221,727; British Pat. No. 564,646 and U.S. Pat. No. 3,964,980.

SUMMARY OF THE INVENTION

In accordance with the present invention, which is based upon the known principle that ethylene oxide is soluble in water, the ethylene oxide contained in these gaseous mixtures used in sterilization processes is absorbed in water, so that the aqueous solution produced thereby can be removed from the remaining constituents contained in the gaseous mixture, which are in themselves less readily soluble in water than is the ethylene oxide.

More particularly, in accordance with the present invention, it has now been discovered that the above discussed difficulties can be overcome by providing a process for the separation of gaseous mixtures of ethylene oxide and relatively inert secondary gaseous components used in sterilization processes in which the process comprises providing a solvent for the ethylene oxide from a solvent source, the solvent comprising water, mixing the gaseous mixture with the solvent so as to produce a liquid phase comprising the ethylene oxide at least partially dissolved in the water, removing the gas phase, primarily comprising the relatively inert secondary gaseous component, from the liquid phase for further processing, separating the ethylene oxide from the water in the liquid phase, and recycling the water to the solvent source for subsequent use as the solvent in this process.

In accordance with a preferred embodiment of the process of the present invention, removing the gas phase from the liquid phase comprises feeding the mixture of the gas phase and the liquid phase to a separating tank including a free liquid surface therein, whereby the gas phase is separated by free gas discharge from the free liquid surface thereof.

In accordance with another embodiment of the process of the present invention, the mixing of the gaseous mixture with the solvent for the ethylene oxide is carried out in a first mixing stage, and the process includes a second mixing stage subsequent to removal of the gas phase from the liquid phase which comprises mixing the gas phase with a further supply of water. Preferably, the second mixing stage includes contacting the gas phase with the further supply of water by countercurrent contact in a water absorption tower. Most preferably, this is accomplished by feeding the further supply of water to an upper portion of the water absorption tower and passing the gas phase upwardly through the water absorption tower. In a most preferred embodiment the further supply of water is fed to first and second locations in the upper portion of the water absorption tower, and a fresh supply of water is fed to the first location, and recycled water from the solvent source is fed to the second location, which is lower in the upper portion of the tower than is the first location.

In accordance with another embodiment of the process of the present invention, separating of the ethylene oxide from the liquid phase includes stripping the ethylene oxide from the water by vigorously blowing a stream of air through the liquid phase.

In accordance with the apparatus of the present invention, it has also been discovered that these problems can be overcome by providing an apparatus for the separation of gaseous mixtures used in such sterilization processes including a solvent source for providing a solvent for the ethylene oxide, the solvent comprising water, mixing means for mixing the gaseous mixture with the solvent so as to provide a liquid phase comprising the ethylene oxide at least partially dissolved in the water and wherein the relatively inert secondary gaseous component remains substantially in the gas phase so it can be readily separated from the liquid phase, removing means for removing the gas phase from the liquid phase for further processing, separating means for separating the ethylene oxide from the water in the liquid phase, and recycling means for recycling the water to the solvent source means for subsequent use as the solvent in this apparatus.

In accordance with a preferred embodiment of the apparatus of the present invention, the solvent source means comprises a water tank, the mixing means comprises pump means, and the removing means comprises a separating tank including a free liquid surface, a gas discharge outlet located above the free liquid surface, and a liquid discharge outlet located below the free liquid surface, whereby the gas phase is separated therein by free gas discharge from the free liquid surface, the gas phase may be withdrawn from the gas discharge outlet, and the liquid phase may be withdrawn from the liquid discharge outlet.

In accordance with another embodiment of the apparatus of the present invention, the gaseous mixture is provided from a plurality of sources, and the apparatus includes combining means for combining the gaseous mixtures provided by these plurality of sources, and the mixing means mixes the gaseous mixtures from the plurality of sources with the solvent.

In accordance with another embodiment of the apparatus of the present invention, a second mixing means is provided for mixing the gas phase removed from the liquid phase with a further supply of water. Preferably, the removing means comprises a separating tank as set forth above, and the second mixing means comprises a water absorption tower including water inlet means at the upper portion of the tower and gas inlet means at the lower portion of the tower, whereby the further supply of water can be delivered to the water inlet means and the gas phase withdrawn from the gas discharge outlet of the separating tank can be delivered to the gas inlet means for countercurrent contact in the tower. In a preferred embodiment thereof, the water inlet means includes first and second water inlets, the first water inlet being located above the second water inlet, and preferably including fresh water supply means for supplying fresh water to the first water inlet and recycled water supply means for supplying recycled water from the solvent source to the second water inlet.

In accordance with another embodiment of the apparatus of the present invention the separating means comprises a stripping tower including liquid phase entrance means for feeding the liquid phase to the stripping tower and creating a liquid flow in a first direction through the tower, and blower means for creating a vigorous gaseous flow in a second direction through said tower, the second direction being countercurrent to the first direction.

A particular advantage of both the process and apparatus of this invention is that the water used as the solvent constitutes an inexpensive solvent which is also environmentally acceptable. To further reduce the cost of the process, however, the water can be recycled in accordance herewith after the ethylene oxide has been wholly or partially removed therefrom.

As is further set forth above, the water can be fed to the gaseous mixture in two stages. In the first stage the recycled water from the solvent source can be fed to the gaseous mixture in order to produce a coarse separation in the separating tank. Subsequently, however, additional ethylene oxide can be separated by conducting the partially cleaned gas to a water absorption tower where it is countercurrently contacted with the water. The water fed to this tower can be fed to the tower at one, two or more points in the tower, and as indicated it is suitable to feed clean water at the highest point in the tower and recycled water at one or more lower points or levels therebelow. By thus feeding clean water in this manner not only is an extremely effective separation of ethylene oxide realized, but in addition a certain amount of compensation for liquid losses in other parts of the system is achieved.

Subsequent to removal of the ethylene oxide from the gaseous mixture, the recovered gaseous constituents can then be compressed and/or cooled, and this can be done in either two or more stages. Furthermore, the recovered gaseous constituents may also need to be dried, which can be done either in the gas phase or in the liquid phase.

In accordance with one of the embodiments of the apparatus discussed above, several sources of the gaseous mixture being treated can be appropriately connected to a common point for simultaneous or successive treatments therewith. These sources can thus be either directly connected to the point in the plant or apparatus where the initial or first mixing with the solvent takes place, or through one or more pre-treatment steps to one or more subsequent points in the process. For example, the water containing ethylene oxide obtained from the coarse separation of each source of gaseous mixtures can be collected, for example, at a joint collecting point, while at the same time the gaseous mixture remaining after the coarse separation step is delivered to a subsequent point in the system for further cleaning.

Also, in connection with the use of two or more sources of gaseous mixtures the apparatus should include an intermediate storage tank for the intermediate storage of liquids containing dissolved gases obtained from these different sources. In this manner, uniform loading is achieved so that no component has to be designed for the otherwise maximum possible load.

BRIEF DESCRIPTION OF THE DRAWING

The present invention will be described in more detail with reference to the following detailed description, and the attached drawing, in which a preferred embodiment of the subject of the present invention is shown in the form of a schematic diagram, with an alternative embodiment in phantom view thereon.

DETAILED DESCRIPTION

The drawing shows a preferred embodiment of the subject of the present invention.

Referring to the drawing, a first gas source 1, e.g. a gas sterilizing oven is shown, used, for example, for sterilizing plastic articles in the medical field, which do not tolerate heat or radiation sterilization.

A valve aggregate 2 is shown, comprising three valves 2a, 2b and 2c, and two pressure-detecting regulators P. It is the object of valve aggregate 2 to reduce and thereby equalize the flow from the source 1, so that an even flow is obtained therefrom during the greater part of the recovery cycle, and even though the pressure drops while the gas mixture is being pumped from the source 1 by means of pump 3. This pump 3 at the same time accomplishes mixing of the gas mixture pumped out of source 1 with the liquid, which is delivered via a valve 3a and a valve system 8 from a liquid source 6. If it is ethylene oxide which is to be removed, this liquid will be water, to which may be added, however, various additives for particular purposes. From the pump 3 the mixture of gas and liquid is then pumped via duct 3b to a separating tank 4, with a free liquid surface 4a. The tank 4 includes two outlets, namely a lower outlet 4b for liquid with gas dissolved therein, and an upper outlet 4c for the non-absorbed gas constitutent(s). These constituents are subsequently delivered via valve 4c' to a liquid absorption tower 12. Alternatively, however, this gaseous mixture may be removed from the system via valve 4d. This is done, for example, in connection with the flushing of the gas sterilizing oven 1. Such flushing is carried out by means of air, and the flushed-out gas thus becomes so diluted that it becomes unprofitable from a point of view of recovery. From outlet 4b the liquid phase with the gas dissolved therein is pumped by means of pump 5, via non-return valve 5d, to collecting tank 9. To this tank clean or cleaned (recycled) liquid can be delivered via duct 9a from the liquid source 6, which also provides the liquid pump 3 with liquid. Delivery of liquid to tank 9 takes place in this case via distributing valve system 8, and non-return valve 8a. The tank 9 can also be vented via outlet 9b and non-return valve 9c to a chimney or the like. The liquid with gas absorbed therein delivered to tank 9 is then passed via outlet 9d, by means of a pump 10, and via non-return valve 10a, to a degassing installation 13-15, which is described in greater detail below.

The gas separated in separating tank 4 is delivered via outlet 4c and valve 4c' to a gas absorption tower 12. A level control means, schematically designated as 12a, is arranged so as to increase or reduce the pumping of liquid from tower 12 by means of pump 11, via a non-return valve 11a, to tank 9. Liquid is fed to the tower 12 at an upper point or an upper level 12b. If ethylene oxide is to be removed, this liquid constitutes clean water, which is fed via valves 12c and 12d. At a lower point 12e in the tower further liquid is fed via valve 12f. This further liquid can be delivered appropriately from the liquid source 6 via valve system 8 and separate control valve 8b.

After cleaning in the gas absorption tower 12, the cleaned gas is delivered via upper outlet 12g to a compression chamber 17. This is done via pressure control means 16, which insures an even flow through the chamber 17 by the opening of a gas return duct 16a if the pressure before the chamber 17 happens to be too low. In this way, it is insured that the tower 12, for example, is not subjected to a harmful partial vacuum. The compressed gas is then delivered via safety valve 17a to heat exchanger 18, for the purpose of cooling. To heat exchanger 18 clean water is delivered via valve 18a. Furthermore, a liquid trap 19 is provided for the collection of any liquid precipitated from the gas in heat exchanger 18.

Subsequently, the gas is delivered to a further compression chamber 17', and from there through a line which includes a further safety valve 17a' to a second heat exchanger 21, to which clean water is fed via valve 21a. The recycling duct 16a is connected to a point inside the heat exchanger 21 where the gas has not yet been condensed.

The condensed gas is then passed from the heat exchanger 21 via shutoff valve 21a to a storage tank 22, whose pressure is controlled by means of pressure control device 23. With the help of a liquid pump 26, the gas is then pumped to a phase separator 27, which may be provided with known coarse separating filters, e.g. the DUSEC Coalescer, from Knit Mesh Limited. With the aid of these filters, a substantial portion of the remaining water is separated via valve 27a. The partially dried gas in turn, passes through valve 27b, with the help of a liquid pump 28, for final drying by means of a so-called molecular sieve 20. Such a sieve may operate based on the fact, for example, that freon has a molecular size 3 times greater than that of water, so that the water can thus be removed with the help of a suitable drying medium having a pore size such that the water can penetrate, but the freon cannot.

Finally, the gas is delivered to gas holders 24. To make it possible to use the same gas holders to which the earlier gas mixtures were delivered, means are provided by which the gas holders can be evacuated, i.e. via valve 24a and duct 24b, with a further valve 24c, and with the help of the pump 3, before they are again filled with the cleaned part of the original gas mixture.

The designations 1a and 1b refer to further possible gas sources, e.g. other sterilizing ovens, which via their own valve systems 2 and pumps 3, together with coarse separation tanks 4, and further pumps 5, can be connected to a common collecting tank 9. At the same time, the gas separated in the coarse separating tanks 4 can be delivered via valves 4c'' and 4c''' directly to the liquid absorption tower 12. In this manner, the plant as a whole can be loaded uniformly without having to be designed for its theoretically possible maximum capacity.

From collecting tank 9 the liquid with admixed gas is then conducted via outlet 9d, by means of pump 10, and via valve 10a, to the gas separation installation 13-15. In the example shown, this consists of a stripping tower 14 (or desorption or cooling tower), through which the liquid is passed countercurrent to a vigorous air flow produced by blower 13, as a result of which the gas absorbed in the liquid is degassed and passes through jet hood 15. Alternatively, of course, this part of the original gas mixture may also be retained for further cleaning and/or reutilization.

In view of the fact that liquid can be fed to the collecting tank not only from separating tanks 4, but also directly from the liquid source 6, the degassing installation can operate continuously under a substantially constant load.

Finally, designations 6a and 6b refer, respectively, to a level control system 6a, by the use of which clean liquid can be delivered to the liquid source 6, and a draining valve 6b, by the use of which liquid can be continuously or intermittently discharged, as required, so as to prevent any excessive increase in the concentration of salts or the like owing to evaporation in the system, such as in the gas separation installation 13-15.

An alternative embodiment is indicated in the drawing by phantom lines. In accordance with this embodiment, the gas is dried in the gas phase with the help of two molecular sieves 20, connected in parallel, before it is compressed in the compressor chamber 17' and cooled to liquid form in the heat exchanger 21. In such an embodiment, the storage tank 22 can be connected directly to the gas holder 24.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

What we claim is:

1. A process for the separation of gaseous mixtures used in sterilization processes, such gaseous mixtures including ethylene oxide and at least one chlorofluorocarbon gaseous component, said process comprising the steps of providing an aqueous solvent for said ethylene oxide from a solvent source, mixing said gaseous mixture with said aqueous solvent so as to produce a liquid phase comprising said ethylene oxide at least partially dissolved in said aqueous solvent, said at least one chlorofluorocarbon gaseous component being less soluble in said aqueous solvent than is said ethylene oxide, whereby said at least one chlorofluorocarbon gaseous component remains substantially in the gas phase and is therefore readily separable from said liquid phase, removing said gas phase from said liquid phase, recovering chlorofluorocarbons from said gaseous phase, separating said ethylene oxide from said aqueous solvent in said liquid phase, and recycling said aqueous solvent to said solvent source for subsequent use as said aqueous solvent.

2. The process of claim 1 wherein said at least one chlorofluorocarbon gaseous component comprises a mixture of chlorofluorocarbons.

3. The process of claim 1 including drying said gas phase removed from said liquid phase.

4. The process of claim 1 including cooling said gas phase removed from said liquid phase.

5. The process of claim 1 including compressing said gas phase removed from said liquid phase.

6. The process of claim 1 wherein said removing of said gas phase from said liquid phase comprises feeding said mixture of said gas phase and said liquid phase to a separating tank including a free liquid surface therein, whereby said gas phase is separated by free gas discharge from said free liquid surface thereof.

7. The process of claim 1 wherein said mixing of said gaseous mixture with said aqueous solvent for said ethylene oxide comprises a first mixing stage, and including a second mixing stage subsequent to said removing of said gas phase from said liquid phase comprising mixing said gas phase with a further supply of water.

8. The process of claim 7 wherein said removing of said gas phase from said liquid phase comprises feeding said mixture of said gas phase and said liquid phase from said first mixing stage to a separating tank including a free liquid surface therein, whereby said gas phase is separated by free gas discharge from said free liquid surface thereof, and wherein said second mixing stage comprises contacting said gas phase with said further supply of water by countercurrent contact in a water absorption tower.

9. The process of claim 8, wherein said countercurrent contact comprises feeding said further supply of water to an upper portion of said water absorption tower and passing said gas phase upwardly through said water absorption tower.

10. The process of claim 9 wherein said feeding of said further supply of water to said upper portion of said water absorption tower comprises feeding said further supply of water to first and second locations at said upper portion of said water absorption tower, said first location being higher in said tower than said second location.

11. The process of claim 10 wherein said feeding of said further supply of water to said first location in said water absorption tower comprises feeding a fresh supply of water thereto, and wherein said feeding of said further supply of water to said second location in said water absorption tower comprises feeding said recycled water from said solvent source thereto.

12. The process of claim 1 wherein said separating of said ethylene oxide from said water in said liquid phase comprises stripping said ethylene oxide from said water by vigorously blowing a stream of air through said liquid phase.

13. The process of claim 3 including cooling said gas phase removed from said liquid phase prior to said drying step.

14. The process of claim 13 including compressing said gas phase removed from said liquid phase prior to said cooling step.

15. The process of claim 4 wherein said cooling of said gas phase removed from said liquid phase is carried out so as to condense said gas phase and produce a liquid phase therefrom.

16. The process of claim 15 including drying said liquid phase produced from said condensation of said gas phase.

* * * * *